US009394342B2

(12) United States Patent
Mehta et al.

(10) Patent No.: US 9,394,342 B2
(45) Date of Patent: Jul. 19, 2016

(54) METHODS OF TREATING MEDICAL CONDITIONS USING PEPTIDES

(71) Applicant: Keybioscience AG, Stans (CH)

(72) Inventors: Nozer M. Mehta, Randolph, NJ (US); Amy Sturmer, Towaco, NJ (US); William Stern, Tenafly, NJ (US)

(73) Assignee: KeyBioscience AG, Stans (CH)

( * ) Notice: Subject to any disclaimer, the term of this patent is extended or adjusted under 35 U.S.C. 154(b) by 0 days.

(21) Appl. No.: 13/930,438

(22) Filed: Jun. 28, 2013

(65) Prior Publication Data
US 2014/0073561 A1 Mar. 13, 2014

Related U.S. Application Data

(63) Continuation of application No. 13/544,256, filed on Jul. 9, 2012, now Pat. No. 8,497,347, which is a continuation of application No. 13/295,906, filed on Nov. 14, 2011, now Pat. No. 8,217,139, which is a continuation of application No. 12/692,502, filed on Jan. 22, 2010, now Pat. No. 8,076,291.

(60) Provisional application No. 61/205,750, filed on Jan. 22, 2009.

(51) Int. Cl.
*A61K 38/23* (2006.01)
*C07K 14/585* (2006.01)
*C07K 14/00* (2006.01)
*A61K 38/00* (2006.01)

(52) U.S. Cl.
CPC ............... *C07K 14/00* (2013.01); *C07K 14/585* (2013.01); *A61K 38/00* (2013.01)

(58) Field of Classification Search
CPC ....... A61K 38/00; A61K 38/23; A61K 45/06; C07K 14/575; C07D 487/04
See application file for complete search history.

(56) References Cited

U.S. PATENT DOCUMENTS

| | | | |
|---|---|---|---|
| 4,708,934 A | | 11/1987 | Gilligan et al. |
| 4,764,589 A | | 8/1988 | Orlowski |
| 5,175,146 A | | 12/1992 | Basava et al. |
| 5,527,771 A | * | 6/1996 | Beaumont et al. ............ 514/6.9 |
| 5,536,812 A | | 7/1996 | Noda et al. |
| 5,580,953 A | * | 12/1996 | Albrecht et al. ............ 530/303 |
| 5,688,784 A | | 11/1997 | McNeill et al. |
| 6,420,561 B1 | | 7/2002 | Haruta et al. |
| 8,076,291 B2 | | 12/2011 | Mehta et al. |
| 8,217,139 B2 | | 7/2012 | Mehta et al. |
| 8,378,067 B2 | | 2/2013 | Mehta et al. |
| 2005/0197287 A1 | | 9/2005 | Mack et al. |
| 2006/0127995 A1 | | 6/2006 | Consalvo |
| 2006/0292672 A1 | | 12/2006 | Miller et al. |
| 2008/0207512 A1 | | 8/2008 | Roth et al. |
| 2008/0274952 A1 | | 11/2008 | Soares et al. |
| 2009/0048157 A1 | | 2/2009 | Azria |
| 2012/0302497 A1 | | 11/2012 | Mehta et al. |

FOREIGN PATENT DOCUMENTS

| | | |
|---|---|---|
| EP | 0308067 | 3/1989 |
| EP | 0382403 | 8/1990 |
| JP | 2000290295 | 10/2000 |
| WO | 9624618 | 8/1996 |
| WO | 9640196 | 12/1996 |
| WO | 2006-083254 | 8/2006 |
| WO | WO 2006083254 A1 * | 8/2006 |

OTHER PUBLICATIONS

Siligardi et. al. European Journal of Biochemistry. May 1, 1994, vol. 221 Issue 3, p. 1117. 9p.*
NIH, Type I diabetes. http://www.nlm.nih.gov/medlineplus/ency/article/000305.htm, last visited Aug. 5, 2015.*
Harald John et al., "N-Terminal Acetylation Protects Glucagon-Like Peptide GLP-1-(7-34)-Amide from DPP-IV-Mediated Degradation Retaining cAMP- and Insulin-Releasing Capacity", European Journal of Medical Research, (Feb. 2008) 13:73-78.
Heinrich Brinkmeier et al., "An endogenous pentapeptide acting as a sodium channel blocker in inflammatory autoimmune disorders of the central nervous system", Nature Medicine, (Jul. 2000) 6(7):808-811.
Piyali Dasgupta et al., "N-Terminal Acylation of Somatostatin Analog with Long Chain Fatty Acids Enhances Its Stability and Anti-Proliferative Activity in Human Breast Adenocarcinoma Cells", Biol. Pharm. Bull. (Jan. 2002) 25 (1):29-36.
Pierrette Gaudreau et al., "Affinty of Human Growth Hormone-Releasing Factor (1-29)NH2 Analogues for GRF Binding Sites in Rat Adenopituitary", Journal of Medical Chemistry (May 1992) 35(10):1864-1869.
C.M. Mack et al., "Davalintide (AC2307), a novel amylin-mimetic peptide: enhanced pharmacological properties over native amylin to reduce food intake and body weight", Original Article—International Journal of Obesity, (2009) pp. 1-11.
E. Del Prete et al., "Effects of amylin and salmon calcitonin on feeding and drinking behavior in pygmy goats", Physiology & Behavior, (2002) 75:593-599.
Eva Tavares et al., "N-Procalcitonin: Central Effects on Feeding and Energy Homeostasis in Rats", Endocrinology, (2007) 148(4):1891-1901.
John F. Deakin et al., "Influence of N-terminal acetylation and C-terminal proteolysis on the analgesic activity of β-endorphin", Biochem. J. (Sep. 1980), 189(Part 3):501-506.
Nozer M. Mehta, "Oral Delivery and Recombinant Production of Peptide Hormones, Part II: Recombinant Production of Therapeutic Peptides", Biopharm. International, (Jul. 2004 ) pp. 44-46.
Martha V. L. Ray et al., "Production of salmon calcitonin by direct expression of a glycine-extended precursor in *Escherichia coli* ", Protein Expression & Purification, (2002) 26:249-259.

(Continued)

*Primary Examiner* — Jeanette Lieb
(74) *Attorney, Agent, or Firm* — Benjamin A. Adler

(57) ABSTRACT

The present invention provides peptides and pharmaceutical compositions thereof for appetite suppression and weight control. Preferred peptides are calcitonin analogs, preferably with specific amino acid changes to make the peptide more amylin-like.

12 Claims, 6 Drawing Sheets

(56) References Cited

OTHER PUBLICATIONS

Martha V. L. Ray et al., "Production of Recombinant Salmon Calcitonin by In Vitro Amidation of an *Escherichia coli* Produced Precursor Peptide", Biotechnology, (Jan. 1993) 11:64-70.
Mark J. Perlow et al., "Calcitonin Reduces Feeding in Man, Monkey and Rat", Pharmacology Biochemistry & Behavior, (Feb. 1979) 12:609-612.
Nicholas T. Bello et al., "Salmon calcitonin reduces food intake through changes in meal sizes in male rhesus monkeys", Articles in PresS. Am J Physiol Regul Integr Comp Physiol, (May 14, 2008), doi:10.1152/ajpregu.90327.2008,pp. 1-25.
Louis Aronne, et al., "Progressive Reduction in Body Weight after Treatment with the Amylin Analog Pramlintide in Obese Subjects: A Phase 2, Randomized, Placebo-Controlled, Dose-Escalation Study", The Journal of Clinical Endocrinology & Metabolism, (2007) 92(8):2977-2983.
Michael J. Twery et al., "Analogue separates biological effects of salmon calcitonin on brain and renal cortical membranes", European Journal of Pharmacology, (1988) 155:285-292.
M.J. Twery et al., "Neuronal membrane sensitivity to a salmon calcitonin analogue with negligible ability to lower serum calcium", Neuroscience Letters, (1988) 86:82-88.
Manfred Hallschmid et al., "Manipulating central nervous mechanisms of food intake and body weight regulation by intranasal administration of neuropeptides in man", Physiology & Behavior, (2004) 83:55-64.
Peter Y. Wielinga et al., "The acute effect of amylin and salmon calcitonin on energy expenditure", Physiology & Behavior, (2007) 91:212-217.
Prasanth K. Chelikani et al., "Inravenous Infusion of Peptide YY(3-36) Potently Inhibits Food Intake in Rats", Endocrinology (2005) 146(2):879-888.
Roger D. Reidelberger et al., "Effects of amylin-related peptides on food intake, meal patterns, and gastric emptying in rats", Am J Physiol Regulatory Integrative Comp Physiol, (2002) 282:R1395-R1404.
T.A. Lutz et al., "Amylin receptors mediate the anorectic action of salmon calcitonin (sCT)", Peptides, (2000) 21:233-238.
Sandra Eiden et al., "Salmon calcitonin—a potent inhibitor of food intake in states of impaired leptin signalling in laboratory rodents" Journal of Physiology, (2002) 541(3):1041-1048.
Prasanth K. Chelikani et al. "Effects of Intermittent Intraperitoneal Infusion of Salmon Calcitonin on Food Intake and Adiposity in Obese Rats", Articles in PresS. Am J Physiol Regul Integr Comp Physiol (Aug. 29, 2007), doi:10.1152/ajpregu.00386.2007, pp. 1-41.
Prasanth K. Chelikani et al., "Intravenous infusion of glucagon-like peptide-1 potently inhibits food intake, sham feeding, and gastric emptying in rats", Articles in PresS. Am J Physiol Regul Integr Comp Physiol (Feb. 17, 2005), doi:10.1152/ajpregu.00870.2004, pp. 1-50 pages.
Mayumi Shimizu et al., "Enhancement of Antimicrobial Activity of Neuropeptide Y by N-Terminal Truncation", Antimicrobial Agents and Chemotherapy, (Oct. 1998) 42(10):2745-2746.
S. T. Prigge et. al., "New insights into copper monooxygenases and peptide amidation: structure, mechanism, and function", CMLS, Cell. Mol. Life Sci., (2000) 57:1236-1259.
Notification of Transmittal of the International Search Report and the Written Opinion of the International Searching Authority dated Jul. 29, 2010, issued in corresponding International Application No. PCT/US2010/021872.
Bin Yang et al., "Synthesis of Salmon Calcitonin Analogs Using F-moc based Chemistry on MBHA Resins", Chinese Chemical Letters, (1999) 10(7):549-552.
M. Zarandi et al., "Synthesis and biological activities of highly potent antagonists of growth hormone-releasing hormone", Proc. Natl. Acad. Sci. USA, (Dec. 1994) 91:12298-12302.
Official Office Action issued in connection with U.S. Appl. No. 13/295,936 mailed Apr. 27, 2012.
Official Office Action issued in connection with U.S. Appl. No. 13/544,256 mailed Oct. 25, 2012.
Official Office Action issued in connection with U.S. Appl. No. 13/295,936 mailed Aug. 8, 2012.

\* cited by examiner

METHODS OF TREATING MEDICAL CONDITIONS USING PEPTIDES

CROSS-REFERENCE TO RELATED APPLICATION(S)

This application is a continuation of U.S. application Ser. No. 13/544,256, filed on Jul. 9, 2012, which is a continuation of U.S. Pat. No. 8,217,139, issued on Jul. 10, 2012, which is a continuation of U.S. Pat. No. 8,076,291, issued on Dec. 13, 2011, which claims the benefit of and priority to U.S. Provisional Application Ser. No. 61/205,750, filed on Jan. 22, 2009, each of these applications is hereby incorporated herein by reference in its entirety for the teachings therein.

BACKGROUND OF THE INVENTION

1. Field of the Invention

The present invention relates to peptides (and pharmaceutical compositions containing them) for suppressing appetite, and to their use for treating and/or preventing overweight conditions or obesity in susceptible warm-blooded animals, including humans. In particular, the invention relates to certain calcitonin analogs.

2. Background of the Related Art

Overweight condition or obesity is a well-known risk factor for many diseases such as cardiovascular diseases, hypertension and diabetes. Moreover, personal appearance plays an important part in the overall well-being of many people. An overweight condition may also reduce or limit an individual's ability to participate in desired physical activities.

Common treatment and prevention programs include various diets (including food restriction diets), weight loss programs and exercise, which provide varying degrees of success that have not proven adequate for many people. Numerous pharmaceutical compositions have been tried in the prior art, sometimes with significant undesirable side effects.

Desirable reduction of food intake is made difficult by natural appetite increase which frequently accompanies the intake reduction. This results in significant patient noncompliance with regimens involving reduction of food intake. Thus, there is a need in the art for safe and effective appetite suppressants.

Calcitonins are known to suppress appetite, but are potent bone anti-resorptive agents. Their use as appetite suppressants is therefore limited because of their effect on bone, which would not be desirable for more general use in a weight control regimen.

SUMMARY OF THE INVENTION

It is accordingly an object of the present invention to provide calcitonin analogs which retain significant appetite suppressant activity but which are less potent bone anti-resorptive agents than calcitonin.

It is another object of the invention to provide novel peptides (and pharmaceutical compositions containing them) for use as appetite suppressants.

It is another object of the invention to provide methods of suppressing appetite.

It is another object of the invention to provide methods of treating and/or preventing an overweight condition and/or obesity.

In one embodiment, the present invention provides a peptide whose amino acid sequence has at least 84 percent identity to the amino acid sequence of either salmon or eel calcitonin, wherein at least one amino acid residue of said peptide is different from the corresponding amino acid residues of both salmon and eel calcitonin and is identical to the corresponding amino acid residue of human amylin.

In another embodiment, the present invention provides a peptide whose amino acid sequence is at least 93 percent identical to SEQ ID NO:1, wherein said peptide is not eel or salmon calcitonin or human amylin.

In another embodiment, the present invention provides a peptide whose amino acid sequence is at least 93 percent identical to SEQ ID NO:2, wherein said peptide is not eel or salmon calcitonin or human amylin.

In another embodiment, the present invention provides a peptide having the amino acid sequence set forth in SEQ ID NO:1 wherein (i) residue 26 may be either asparagine or aspartic acid, (ii) residue 29 may be either serine or alanine, and (iii) either residue 30 is not glycine or residue 32 is not proline.

In another embodiment, the present invention provides a peptide having the amino acid sequence set forth in SEQ ID NO:3.

In another embodiment the present invention provides a peptide having the amino acid sequence set forth in SEQ ID NO:4.

In another embodiment the present invention provides a peptide having the amino acid sequence set forth in SEQ ID NO:2 wherein: (i) residue 25 may be either asparagine or aspartic acid, (ii) residue 28 may be either serine or alanine, and (iii) either residue 29 is not glycine or residue 31 is not proline.

In another embodiment, the present invention provides a peptide having the amino acid sequence set forth in SEQ ID NO:3, except that the leucine at position 16 is omitted (thus resulting in SEQ ID NO:5).

In another embodiment, the present invention provides a peptide having the amino acid sequence set forth in SEQ ID NO:4, except that the leucine at position 16 is omitted (thus resulting in SEQ ID NO:6).

In another embodiment, the present invention provides a peptide having the amino acid sequence set forth in SEQ ID NO:7.

In another embodiment, the present invention provides a peptide having the amino acid sequence set forth in SEQ ID NO:8.

In another embodiment, the present invention provides a peptide having the amino acid sequence set forth in SEQ ID NO:12.

In another embodiment, the present invention provides a peptide having the amino acid sequence set forth in SEQ ID NO:13.

In another embodiment, the present invention provides a peptide having the amino acid sequence set forth in SEQ ID NO:14.

In another embodiment, the present invention provides a pharmaceutical composition comprising any of the peptides of the invention described herein together with a pharmaceutically acceptable excipient, diluent or carrier.

In another embodiment, the present invention provides a method of treating or preventing an overweight condition or obesity comprising administering to a patient in need of such prevention or treatment an amount of any of the peptides of the invention described herein (or a pharmaceutical composition thereof) effective to suppress appetite.

In another embodiment, the present invention provides a method of suppressing appetite comprising administering to a patient in need of such suppression an effective amount of any of the peptides of the invention described herein (or a pharmaceutical composition thereof).

In another embodiment, the present invention provides a method of treating diabetes comprising administering to a patient in need of such treatment a therapeutically effective amount of any of the peptides of the invention described herein (or a pharmaceutical composition thereof).

In another embodiment, the present invention provides a method of treating diabetes comprising administering to a patient in need of such treatment a therapeutically effective amount of any of the peptides of the invention described herein (or a pharmaceutical composition thereof).

There are a number of art-recognized measures of normal range for body weight in view of a number of factors such as gender, age and height. A patient in need of treatment or prevention regimens set forth herein include patients whose body weight exceeds recognized norms or who, due to heredity, environmental factors or other recognized risk factor, are at higher risk than the general population of becoming overweight or obese. In accordance with the invention, it is contemplated that the invention may be used to treat diabetes where weight control is an aspect of the treatment.

As used herein, "percent identity" refers to amino acid sequence without regard to whether a given amino acid is modified with an additional substituent (other than an additional amino acid). For example cysteine is considered identical to acetylcysteine for this purpose. Likewise, for this purpose, a cysteine that has formed a disulfide bridge with another cysteine would be considered identical to a cysteine that has not formed such a bridge. "Percent identity" also contemplates differences in peptide size. For example, a 34-residue peptide that is otherwise identical to a 33-residue peptide (except for its one additional amino acid) is considered herein to be 97 percent identical to the 33-residue peptide.

As those of skill in the art will appreciate, peptides having a plurality of cysteine residues frequently form a disulfide bridge between two such cysteine residues. All such peptides set forth herein are defined as optionally including one or more such disulfide bridges.

The peptides known in the art as Davalintide and Pramlintide are excluded from the scope of the invention.

Except where otherwise stated, the preferred dosage of the active compounds of the invention is identical for both therapeutic and prophylactic purposes. Desired dosages are discussed in more detail, infra, and differ depending on mode of administration.

Except where otherwise noted or where apparent from context, dosages herein refer to weight of active compounds uneffective by pharmaceutical excipients, diluents, carriers or other ingredients, although such additional ingredients are desirably included, as shown in the examples herein. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. A preferred oral dosage form is discussed in more detail, infra, but is not to be considered the exclusive mode of administering the active agents of the invention.

Other features and advantages of the present invention will become apparent from the following non-limiting description of certain preferred embodiments, which refers to the accompanying drawings.

BRIEF DESCRIPTION OF THE DRAWINGS

FIG. 1 is a graph illustrating data from a bioassay comparing cAMP response for a peptide of the invention, SEQ ID NO:3, versus recombinant salmon calcitonin. Rats injected intramuscularly with sCT or UGP281 exhibited significant weight loss when injected for two weeks; whereas, rats injected with the same dose of UGP271 exhibited modest weight loss. UGP281 and UGP271 had identical amino acid sequences except that UGP281 was acylated at the N-terminus with acetate.

DETAILED DESCRIPTION OF PREFERRED EMBODIMENTS OF THE INVENTION

Figure 1:
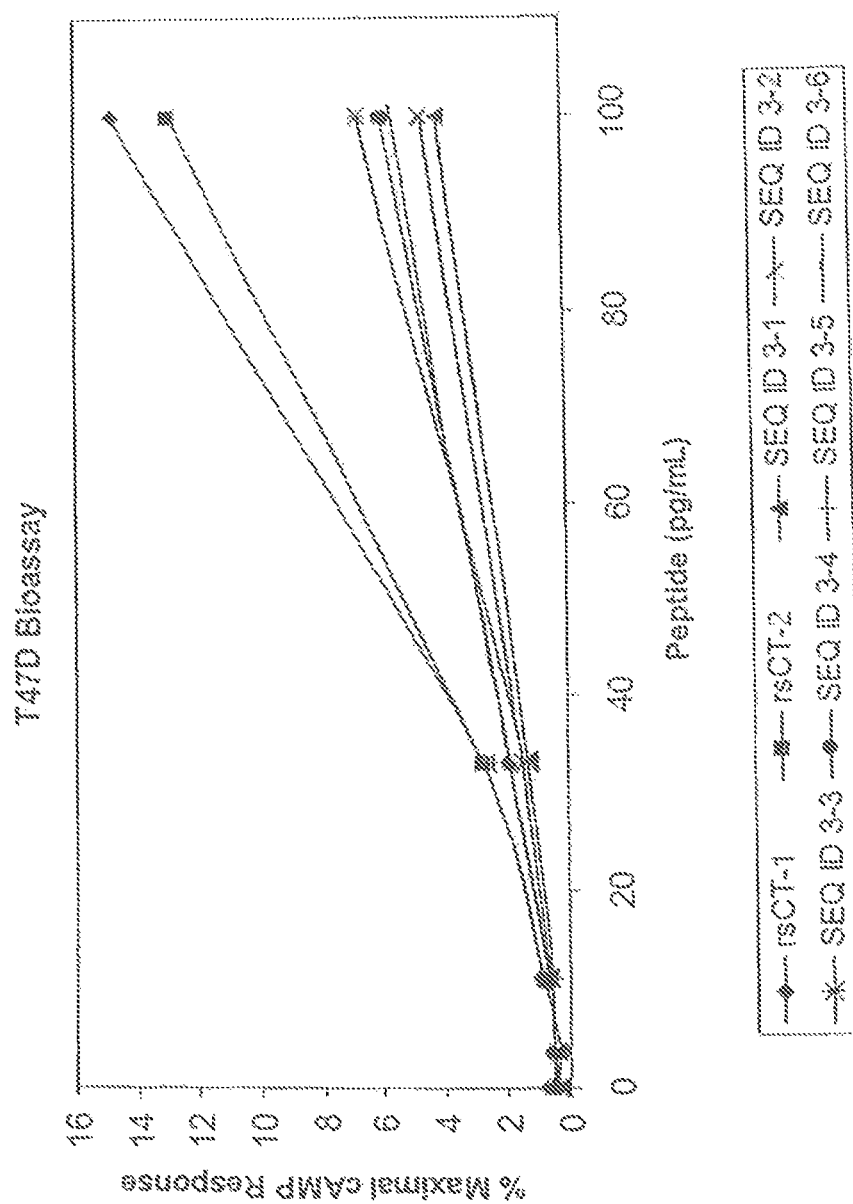
FIG. 1 is a graph illustrating data from a bioassay comparing cAMP response for a peptide of the invention, SEQ ID NO:3, versus recombinant salmon calcitonin. Two replicate bioassay experiments were performed measuring the cAMP response with T47D cells. Each experiment compared three samples of SEQ ID NO:3 to a sample of rsCT.

Preferred peptides of the invention have significant amino acid identity to either salmon or eel calcitonin. Preferably, there is at least 84% identity, and in some embodiments as much as 87%, 90%, 93% or 96% identity to either eel or salmon calcitonin. Preferably, at least one amino acid is modified, relative to both salmon and eel calcitonin, for purposes of decreasing the effect of a peptide of the invention on bone (relative to salmon or eel calcitonin's effect on bone).

In some embodiments, the leucine at position 16 of salmon and eel calcitonin is deleted such that an 31-amino acid peptide results. It is expected that this deletion is likely to desirably decrease the resulting peptide's ability to bind kidney, and osteoclasts relative to natural salmon or eel calcitonin.

While peptides of the invention may exist in free acid form, it is preferred that the C-terminal amino acid be amidated.

Applicants expect that such amidation may contribute to the effectiveness and/or bioavailability of the peptide.

In preferred embodiments, peptides of the invention, whether or not they include the leucine-16 of salmon or eel calcitonin, may have from 1 to 5 positions where their amino acid differs from the corresponding amino acid of both salmon and eel calcitonin. As used herein, the phrase "corresponding amino acid of salmon or eel calcitonin" means the amino acid residue of either salmon or eel calcitonin having the same amino acid position number (relative to its amino terminus) as is being discussed for peptides of the invention where the phrase is used, EXCEPT where the phrase is used in embodiments where leucine-16 is deleted, in which case the "corresponding" amino acid number of salmon or eel calcitonin is one position higher than any position number over 15 in the peptide of the invention.

Preferred positions where the peptide of the invention differs from both eel and salmon calcitonin, for example, are positions 8, 11, 27, 30 and 32. In a peptide of the invention in which leucine-16 has been deleted, relative to natural salmon or eel calcitonin, the foregoing preferred positions of change are positions 8, 11, 26, 29 and/or 31 (corresponding to positions 8, 11, 27, 30 and/or 32 of natural salmon or eel calcitonin). Changes at one or more of these preferred positions, or at other positions, are believed to decrease the effect the peptide would otherwise have on bone, which effect is not desirable in connection with appetite suppression and/or treatment of overweight conditions or obesity.

Without intending to be bound by theory, it is believed that the appetite suppression provided by the peptides of the invention is mediated by binding of the peptides of the invention to the amylin receptor. Thus, in preferred embodiments, the peptides of the invention are desired to be superagonists of the amylin receptor while having diminished binding to the calcitonin receptor. In preferred embodiments, positions where the peptides of the invention differ from the corresponding positions of salmon and/or eel calcitonin preferably utilize the corresponding amino acid of human amylin at the position in question. The phrase "corresponding amino acid of human amylin" as used herein means the amino acid number of human amylin that is the same as the amino acid number of the peptide of the invention being discussed, EXCEPT when the amino acid residue number of the peptide of the invention being discussed is higher than 24, in which case the "corresponding" amino acid residue number of human amylin is 5 higher than the amino acid number of the peptide of the invention. For example, amino acid 24 of the invention corresponds to amino acid number 24 of human amylin, while amino acid 25 of the invention corresponds to amino acid number 30 of human amylin. In embodiments of the invention wherein leucine-16 is omitted, the "corresponding numbers between the invention and human amylin are identical through the first 15 residues, differ by one with residues 16-23 (corresponding to residue 17-24 of human amylin), and differ by six beginning with residue number 24 of the peptide of the invention (which "corresponds to residue 30 of human amylin).

One peptide of the invention, the peptide of SEQ ID NO:3, has asparagine at position 30 and tyrosine at position 32 (corresponding to amylin's asparagine-35 and tyrosine-37) instead of the amino acid residues that eel or salmon calcitonin have at positions 30 and 32. Preferred peptide SEQ ID NO:3 otherwise has the same amino acid sequence as does salmon calcitonin at all positions other than positions 30 and 32 where the peptide has been made more amylin-like. In accordance with another preference of the invention, SEQ ID NO:3 is amidated at tyrosine-32.

Pramlintide, commercially available under the trademark SYMLIN, is an analog of amylin which differs from amylin in ways that resist formation of aggregates (which can be a problem with amylin). Accordingly, the present invention contemplates that pramlintide might be utilized in the same way that amylin is utilized herein. Likewise, elcatonin (an analog of eel calcitonin) might be utilized in the same way that eel calcitonin is utilized herein.

Another peptide of the invention is set forth at SEQ ID NO:4 which is similar to SEQ ID NO:3 except that it contains valine at position 27. Valine-27 makes SEQ ID NO:4 more amylin-like (i.e., corresponds to valine-32 in human amylin). Valine-27 also makes SEQ ID NO:4 more closely resemble eel calcitonin (as opposed to salmon calcitonin) which eel calcitonin also has valine at position 27.

In another embodiment, a peptide of the invention may be identical to SEQ ID NO:3 and SEQ ID NO:4, but missing leucine-16.

In another embodiment, a peptide of the invention may have the amino acid sequence set forth at SEQ ID NO:7 or SEQ ID NO:8

For ease of comparison, the amino acid sequences of natural salmon and eel calcitonin are set forth as SEQ ID NO:9 or SEQ ID NO:10, respectively. The amino acid sequence for human amylin is set forth at SEQ ID NO:11.

Figure 6:
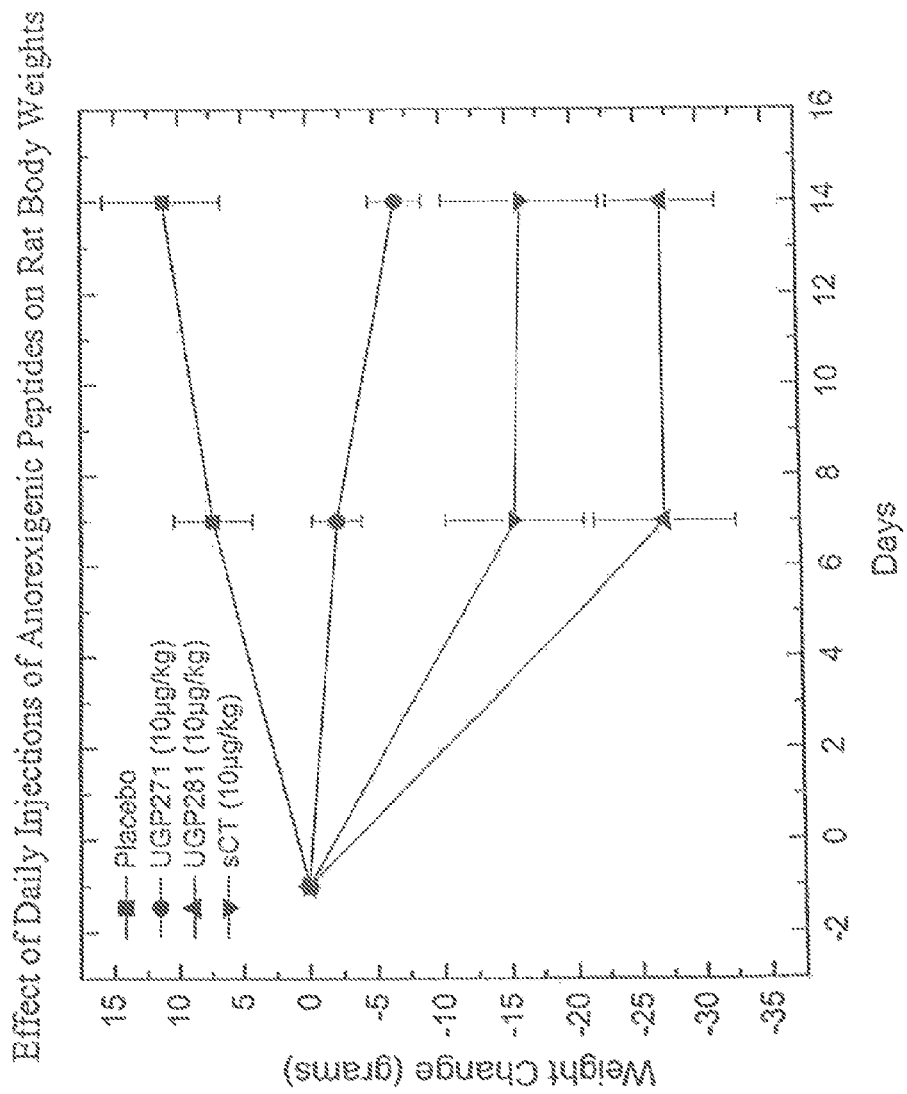
FIG. 6 is a graph illustrating relative weight change by rats injected daily with the same dose of either a placebo, salmon calcitonin, UGP 271 (SEQ ID NO:13) or UGP 281 (SEQ ID NO:14) at 7 and 14 days after commencement of the injection regimen.

In some embodiments, the N-terminal side of the peptides discussed supra is modified to reduce the positive charge of the first amino acid. For example, an acetyl or propionyl group may be substituted on cysteine-1. As illustrated by FIG. 6, improved effectiveness is achieved by such an acetyl substitution. Alternative ways of reducing positive charge include but are not limited to polyethylene glycol-based PEGylation, or the addition of another amino acid such as glutamic acid or aspartic acid at the N-terminus. Alternatively, adding other amino acids to the N-terminus of peptides discussed supra may desirably reduce signal transduction by the calcitonin receptor. Such additional amino acids include but are not limited to lysine, glycine, formylglycine, leucine, alanine, acetyl alanine, and dialanyl.

In some embodiments, peptides discussed supra may be further modified by substituting, for a given amino acid residue, the corresponding amino acid of human amylin.

Recombinant production of peptides of the invention is believed to be more cost effective than other techniques known in the art, although these other techniques may also be used. Preferably, the peptides of the invention are amidated at their C-terminus, although free acid forms are also contemplated. A preferred technique for manufacturing amidated versions of the peptides of the invention is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708,934 and European Patent Publication Nos. 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis. Production of amidated products may also be accomplished using the process and amidating enzyme set forth by Consalvo, et al in U.S. Patent Publication No. 2006/0127995; Miller et al, U.S. Patent Publication No. 2006/

0292672; Ray et al, 2002, Protein Expression and Purification, 26:249-259; and Mehta, 2004, Biopharm. International, July, pp. 44-46.

The production of the preferred amidated peptides may proceed, for example, by producing glycine-extended precursor in *E. coli* as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—$NH_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells, as described in the Biotechnology and Biopharm. articles cited above.

Free acid forms of peptide active agents of the invention may be produced in like manner, except without including a C-terminal glycine on the "precursor", which precursor is instead the final peptide product and does not require the amidation step.

Treatment of Patients

It is preferred that peptides of the invention be administered at adequate dosage to maintain serum levels of the peptide in patients between 5 and 500 picograms per milliliter, preferably between 10 and 250 picograms per milliliter. The serum levels may be measured by radioimmunoassay techniques known in the art. The attending physician may monitor patient response, and may then alter the dosage somewhat to account for individual patient metabolism and response.

While other delivery methods may be used, a peptide of the invention is preferably formulated for oral delivery in a manner known in the art, for example as set forth in U.S. Pat. No. 6,086,018, or U.S. Patent Publication No. 2009/0317462. One preferred oral dosage form in accordance with the invention is set forth in Table 1 below:

TABLE 1

COMPONENTS OF SOLID DOSAGE FORMULATION

| ACTIVE AGENT OR EXCIPIENT | FUNCTION |
|---|---|
| Peptide of SEQ ID NO: 3 | Active agent for appetite suppression |
| Coated Citric Acid | Protease Inhibitor |
| Lauroylcarnitine | Absorption Enhancer |
| Nonionic Polymer | Subcoat |
| Eudragit L30D-55 | Enteric Coat |

The bioavailability achievable in an oral dosage form of this type is expected to be adequate to achieve the above preferred blood levels while using only 100-2000 micrograms of active peptide (in this example SEQ ID NO:3) per dosage form, preferably 200-800 micrograms. When oral formulations of this type and concentration of active ingredient are used, dosages of between 200 and 4000 micrograms per day of active peptide (exclusive of weight of all other ingredients), and preferably between 400 and 1600 micrograms per day, is likely to achieve target blood levels.

These amounts may be provided by either a single daily dosage or multiple dosages. Regardless of the active agent being administered, it is preferred that a single dosage form (for example, a single capsule or tablet) be used at each administration because a single capsule or tablet best provides simultaneous release of the peptide active agent, pH-lowering agent and absorption enhancers. This is highly desirable because the acid is best able to reduce undesirable proteolytic attack on the peptide active agent when the acid is released in close time proximity to release of the active agent.

Near simultaneous release is best achieved by administering all components of the invention as a single pill or capsule. However, the invention also includes, for example, dividing the required amount of the active ingredient among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

Peptides in accordance with the invention may also be delivered by other common techniques in the industry with normal dosage variations between modes of administration. For example, a dosage range between 5 and 100 micrograms per day, (preferably between 10 and 50 micrograms per day, and most preferably between 15 and 35 micrograms per day), is preferred when administered by injection.

In a pharmaceutical composition for injection, the peptide active agent of the invention is preferably present in a concentration between 10 micrograms/mL and 100 micrograms/mL.

Without intending to be bound by theory, the mechanism of action is believed to involve leptin. In some embodiments, leptin may be added to the pharmaceutical composition of the invention, or separately provided.

Efficacy Data

To test whether amino acid substitutions of the invention converted salmon calcitonin to an analog with less binding affinity to the calcitonin receptor (or otherwise less able to undesirably activate calcitonin receptors, the peptide whose amino acid sequence is set forth in SEQ ID NO: 3 was subjected to a bioassay comparing its cAMP response (an indicator of calcitonin receptor activation) to that of salmon calcitonin. As shown in FIG. 1, the data suggest that a calcitonin analog of the invention (SEQ ID NO: 3) is desirably less potent when binding to the calcitonin receptor than is natural salmon calcitonin.

Figure 2:
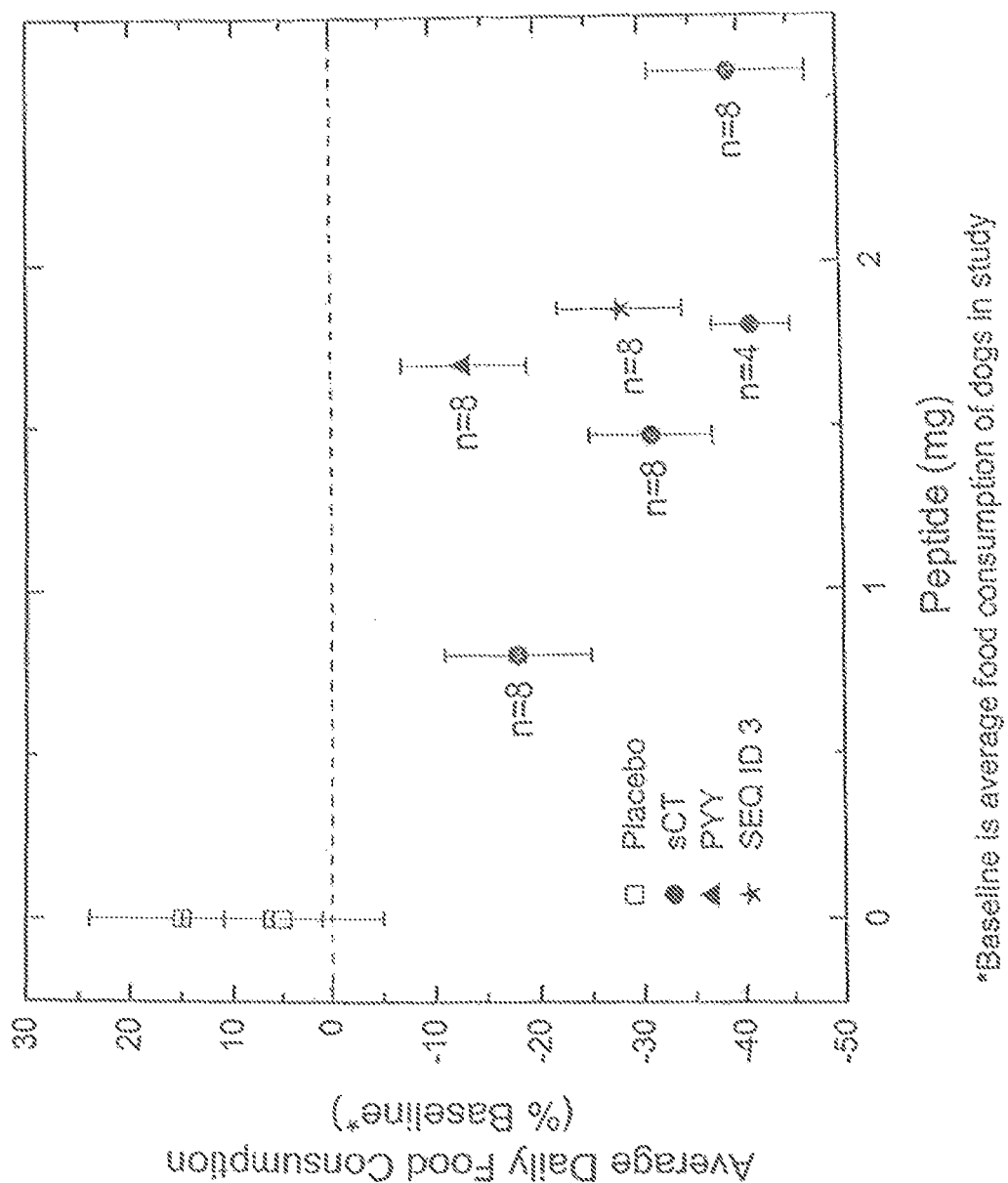
FIG. 2 is a graph illustrating the effect on food consumption provided by SEQ ID NO:3 versus a placebo and two known appetite suppressants in a Beagle dog study. Average daily change in food consumption is shown following administration of oral capsules containing various doses of sCT, PYY or SEQ ID NO:3 given to beagle dogs for four to seven days.

The effect of peptide SEQ ID NO: 3 on food intake was investigated in a placebo controlled crossover study with Beagle dogs. Peptide SEQ ID NO: 3, as well as salmon calcitonin (sCT) and PYY(3-36)$NH_2$ were formulated in enteric-coated capsules for oral delivery. The capsules also contained excipients that inhibit proteases and enhance the absorption of peptides. Placebo capsules contained the same excipients without the peptide. Food and water intake, as well as the weight of the dogs was monitored daily before, during, and after the dosing period. Dogs were allowed access to a known amount of food for an 8 hour period every day, and water was provided ad libitum. As shown in FIG. 2, at equivalent doses, SEQ ID NO: 3 and sCT significantly decreased food intake throughout the week of dosing, whereas PYY exhibited a lesser effect. The food intake of dogs given a placebo remained unchanged.

Figure 3:
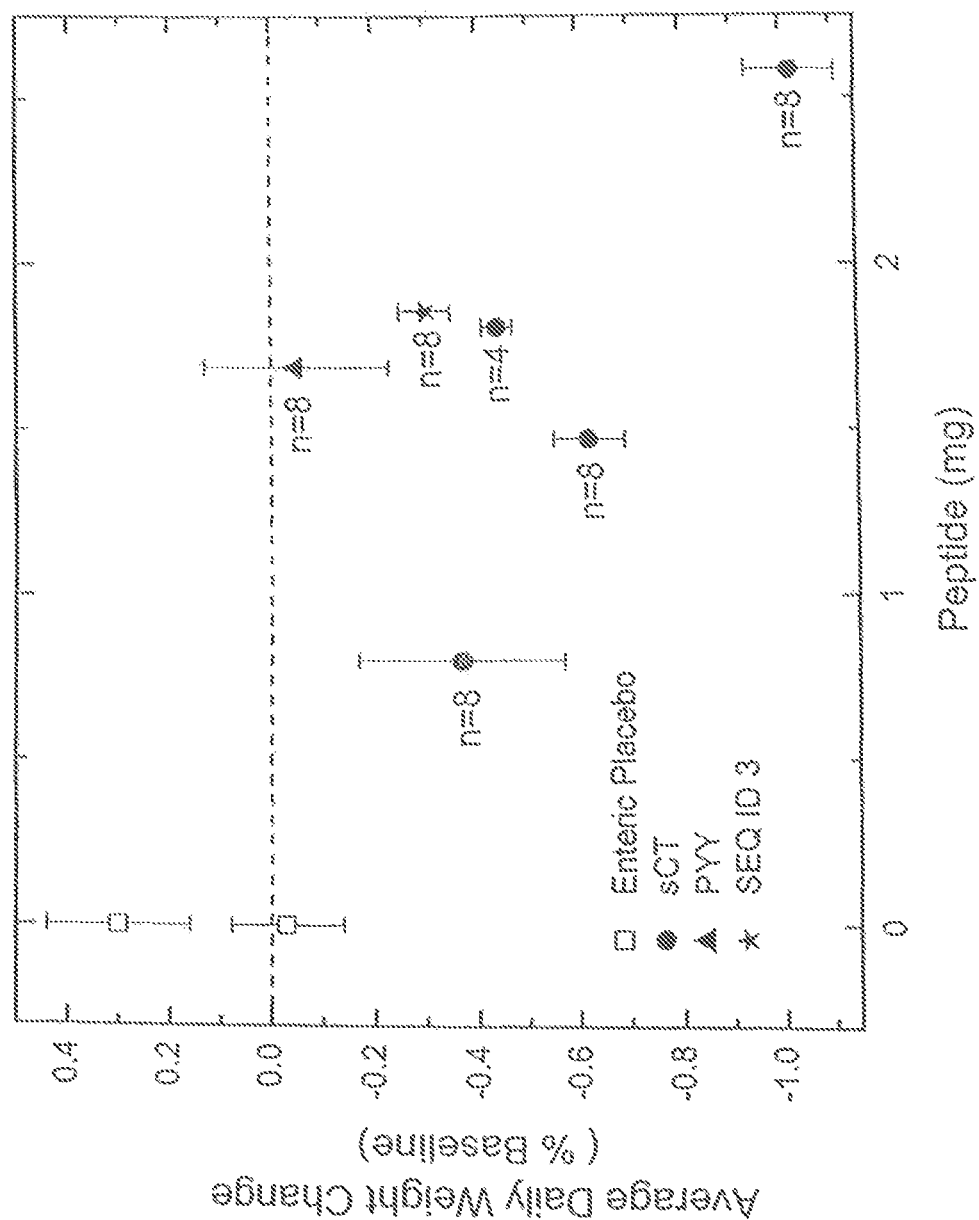
FIG. 3 is a graph illustrating the effect on weight provided by SEQ ID NO:3 versus a placebo and two known appetite suppressants in a Beagle dog study. Average daily change in weight is shown following administration of oral capsules containing various doses of sCT, PYY or SEQ ID NO:3 given to beagle dogs for four to seven days.

As shown in FIG. 3, dogs given SEQ ID NO: 3 and sCT showed a small but significant reduction in weight during the dosing period, whereas dogs receiving the same dose of PYY showed very little change (0.05% per day) in weight. Dogs given placebo capsules exhibited a slight weight increase.

Finally, while water intake was also reduced during the dosing period, it was by a smaller amount than the reduction in food intake. Both food and water intake returned to pre-dose levels during the one week washout period following dosing.

FIGS. 1-3 provide evidence that SEQ ID NO: 3 offers the potential of affecting feeding behavior by reducing food consumption, with a potency that is comparable to that of the bone anti-resorptive peptide sCT.

Figure 4:
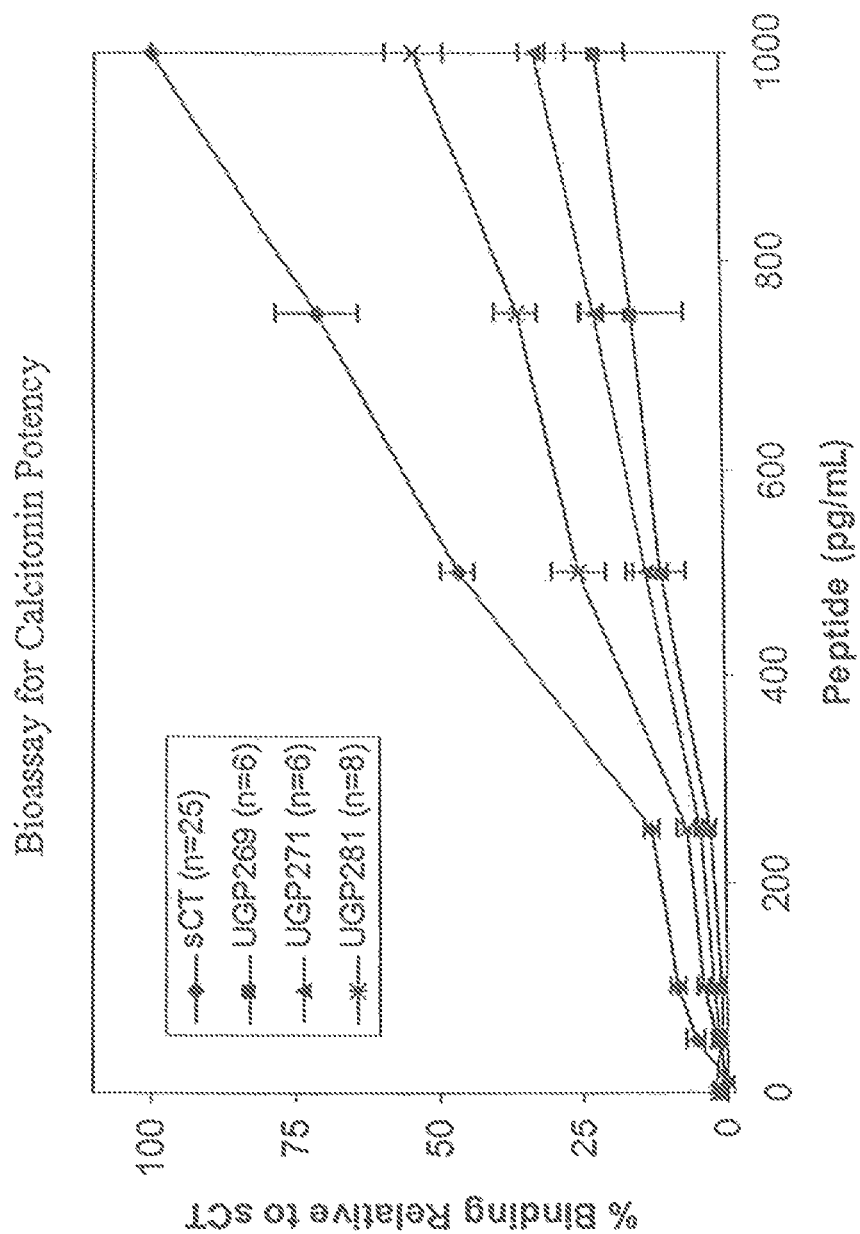
FIG. 4 is a graph illustrating calcitonin-like properties of three peptides of the invention in comparison to salmon calcitonin in an assay that measures binding to calcitonin receptors on T47D cells. The three peptides of the invention are UGP269 (SEQ ID NO:12), UGP 271 (SEQ ID NO:13) and UGP281 (SEQ ID NO:14). The UGP269, UGP271 and UGP281 exhibited less binding to sCT receptors than sCT.

Likewise, FIG. 4 illustrates that UGP269 (SEQ ID NO:12), UGP 271 (SEQ ID NO:13) and UGP281 (SEQ ID NO:14) has less binding affinity for the calcitonin receptor than does salmon calcitonin.

Figure 5:
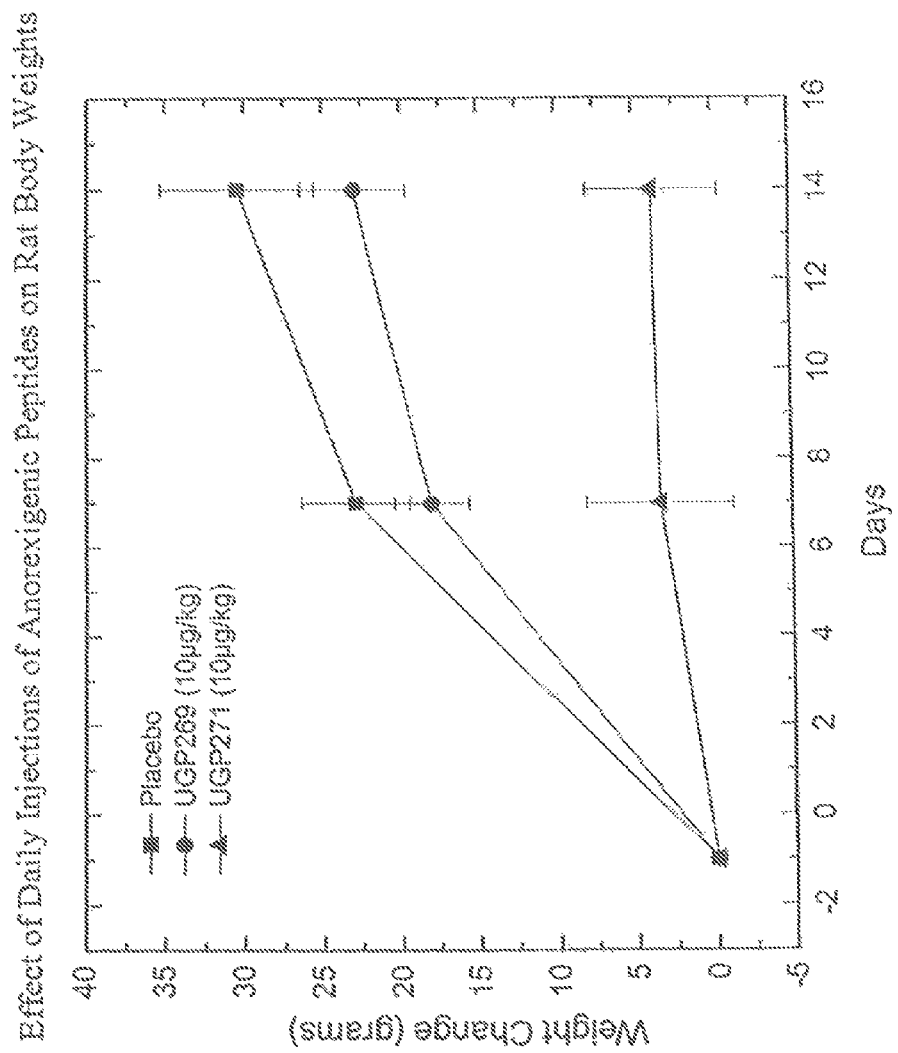
FIG. 5 is a graph illustrating relative weight change by rats injected daily with the same dose of either a placebo, UGP269 (SEQ ID NO:12) or UGP 271 (SEQ ID NO:13), at 7 and 14 days after commencement of the injection regimen. Rats injected with UGP269 showed less weight gain over two weeks than those injected with placebo. Rats injected with the same dose of UGP271 showed no weight gain. UGP271 contained nearly the same sequence of amino acids as UGP269 except for the replacement of three amino acids at positions 26, 27 and 29.

FIGS. 5 and 6 illustrate good effectiveness in weight control by UGP269 (SEQ ID NO:12), UGP 271 (SEQ ID NO:13) and UGP281 (SEQ ID NO:14). FIG. 6 provides evidence of substantial enhancement of efficacy by the acetyl group on cysteine-1 of UGP281 (SEQ ID NO:14).

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A method of treating or reducing the likelihood of an overweight condition in a patient comprising: administering a 32 amino acid peptide to the patient, wherein the amino acid sequence of the peptide is at least 93 percent identical to SEQ ID NO: 1, wherein positions 2-32 of the peptide are identical to positions 2-32 of SEQ ID NO: 1, wherein position 1 of the peptide is cysteine that has been modified with a group selected from one of a succinyl group, an acetyl group or a propionyl group, and wherein position 26 is aspartic acid and position 27 is valine, and wherein position 29 is serine and/or position 30 is asparagine and wherein the body weight of the patient exceeds recognized norms or who, due to heredity, environmental factors or other recognized risk factors, is at higher risk than the general population of becoming overweight or obese.

2. The method of claim 1 wherein the amino acid at position 32 of the peptide is amidated.

3. The method of claim 1 wherein position 32 of the peptide is proline or tyrosine.

4. The method of claim 1 wherein the peptide is a component of a solid oral dosage form, and wherein the solid oral dosage form is selected from one of a capsule or a tablet.

5. The method of claim 1 wherein the peptide is a component of a pharmaceutical composition for injection.

6. The method of claim 1 wherein administering occurs multiple times over a period of time.

7. A method of treating type II diabetes in a patient comprising: administering a 32 amino acid peptide to the patient, wherein the amino acid sequence of the peptide is at least 93 percent identical to SEQ ID NO: 1, wherein positions 2-32 of the peptide are identical to positions 2-32 of SEQ ID NO: 1, and wherein position 1 of the peptide is cysteine that has been modified with a group selected from one of a succinyl group, an acetyl group or a propionyl group, and wherein position 26 is aspartic acid and position 27 is valine, and wherein position 29 is serine and/or position 30 is asparagine.

8. The method of claim 7 wherein the amino acid at position 32 of the peptide is amidated.

9. The method of claim 7 wherein position 32 of the peptide is proline or tyrosine.

10. The method of claim 7 wherein the peptide is a component of a solid oral dosage form, and wherein the solid oral dosage form is selected from one of a capsule or a tablet.

11. The method of claim 7 wherein the peptide is a component of a pharmaceutical composition for injection.

12. The method of claim 7 wherein administering occurs multiple times over a period of time.

* * * * *

SEQUENCE LISTING

```
<160> NUMBER OF SEQ ID NOS: 14

<210> SEQ ID NO 1
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa can be any naturally occurring amino acid
<220> FEATURE:
<221> NAME/KEY: MOD_RES
<222> LOCATION: (32)..(32)
<223> OTHER INFORMATION: Optionally amidated

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Xaa Xaa Gly Xaa Xaa Thr Xaa
            20                  25                  30

<210> SEQ ID NO 2
<211> LENGTH: 31
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MOD_RES
<222> LOCATION: (31)..(31)
<223> OTHER INFORMATION: Optionally amidated

<400> SEQUENCE: 2

Cys Ser Asn Leu Ser Thr Cys Val Leu Gly Lys Leu Ser Gln Glu His
1               5                   10                  15
```

```
Lys Leu Gln Thr Tyr Pro Arg Thr Xaa Xaa Gly Xaa Xaa Thr Xaa
            20                  25                  30
```

<210> SEQ ID NO 3
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (32)..(32)
<223> OTHER INFORMATION: AMIDATION

<400> SEQUENCE: 3

```
Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30
```

<210> SEQ ID NO 4
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (32)..(32)
<223> OTHER INFORMATION: AMIDATION

<400> SEQUENCE: 4

```
Cys Ser Asn Leu Ser Thr Cys Val Leu Gly Lys Leu Ser Gln Glu Leu
1               5                   10                  15

His Lys Leu Gln Thr Tyr Pro Arg Thr Asn Val Gly Ser Asn Thr Tyr
            20                  25                  30
```

<210> SEQ ID NO 5
<211> LENGTH: 31
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (31)..(31)
<223> OTHER INFORMATION: AMIDATION

<400> SEQUENCE: 5

```
Cys Ser Asn Leu Ser Thr Cys Val Leu Gly Lys Leu Ser Gln Glu His
1               5                   10                  15

Lys Leu Gln Thr Tyr Pro Arg Thr Asn Thr Gly Ser Asn Thr Tyr
            20                  25                  30
```

<210> SEQ ID NO 6
<211> LENGTH: 31
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (31)..(31)
<223> OTHER INFORMATION: AMIDATION

```
<400> SEQUENCE: 6

Cys Ser Asn Leu Ser Thr Cys Val Leu Gly Lys Leu Ser Gln Glu His
1               5                   10                  15

Lys Leu Gln Thr Tyr Pro Arg Thr Asn Val Gly Ser Asn Thr Tyr
            20                  25                  30

<210> SEQ ID NO 7
<211> LENGTH: 31
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (31)..(31)
<223> OTHER INFORMATION: AMIDATION

<400> SEQUENCE: 7

Cys Ser Asn Leu Ser Thr Cys Ala Leu Gly Arg Leu Ser Gln Glu His
1               5                   10                  15

Lys Leu Gln Thr Tyr Pro Arg Thr Asp Val Gly Ala Asn Thr Tyr
            20                  25                  30

<210> SEQ ID NO 8
<211> LENGTH: 31
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (31)..(31)
<223> OTHER INFORMATION: AMIDATION

<400> SEQUENCE: 8

Cys Ser Asn Leu Ser Thr Cys Ala Leu Gly Arg Leu Ser Gln Glu His
1               5                   10                  15

Lys Leu Gln Thr Tyr Pro Arg Thr Asn Val Gly Ala Asn Thr Tyr
            20                  25                  30

<210> SEQ ID NO 9
<211> LENGTH: 32
<212> TYPE: PRT
<213> ORGANISM: salmon
<220> FEATURE:
<221> NAME/KEY: MOD_RES
<222> LOCATION: (32)..(32)
<223> OTHER INFORMATION: AMIDATION

<400> SEQUENCE: 9

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 10
<211> LENGTH: 32
<212> TYPE: PRT
<213> ORGANISM: Eel
<220> FEATURE:
<221> NAME/KEY: MOD_RES
<222> LOCATION: (32)..(32)
<223> OTHER INFORMATION: AMIDATION
```

```
<400> SEQUENCE: 10

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
                20                  25                  30

<210> SEQ ID NO 11
<211> LENGTH: 37
<212> TYPE: PRT
<213> ORGANISM: Human
<220> FEATURE:
<221> NAME/KEY: MOD_RES
<222> LOCATION: (37)..(37)
<223> OTHER INFORMATION: AMIDATION

<400> SEQUENCE: 11

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Thr Asn Val
                20                  25                  30

Gly Ser Asn Thr Tyr
            35

<210> SEQ ID NO 12
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (1)..(1)
<223> OTHER INFORMATION: disulfide bridge to CYS-7
<220> FEATURE:
<221> NAME/KEY: MOD_RES
<222> LOCATION: (7)..(7)
<223> OTHER INFORMATION: disulfide bridge to CYS-1
<220> FEATURE:
<221> NAME/KEY: MOD_RES
<222> LOCATION: (32)..(32)
<223> OTHER INFORMATION: amidation

<400> SEQUENCE: 12

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
                20                  25                  30

<210> SEQ ID NO 13
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (1)..(1)
<223> OTHER INFORMATION: disulfide bridge to CYS-7
<220> FEATURE:
<221> NAME/KEY: MOD_RES
<222> LOCATION: (7)..(7)
<223> OTHER INFORMATION: disulfide bridge to CYS-1
<220> FEATURE:
<221> NAME/KEY: MOD_RES
<222> LOCATION: (32)..(32)
<223> OTHER INFORMATION: amidation
```

```
<400> SEQUENCE: 13

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Thr Tyr
                20                  25                  30

<210> SEQ ID NO 14
<211> LENGTH: 32
<212> TYPE: PRT
<213> ORGANISM: Artificial
<220> FEATURE:
<223> OTHER INFORMATION: Designed peptide having some homology to salmon
      and eel calcitonin
<220> FEATURE:
<221> NAME/KEY: MOD_RES
<222> LOCATION: (1)..(1)
<223> OTHER INFORMATION: disulfide bridge to CYS-7
<220> FEATURE:
<221> NAME/KEY: MOD_RES
<222> LOCATION: (1)..(1)
<223> OTHER INFORMATION: acetyl
<220> FEATURE:
<221> NAME/KEY: MOD_RES
<222> LOCATION: (7)..(7)
<223> OTHER INFORMATION: disulfide bridge to CYS-1
<220> FEATURE:
<221> NAME/KEY: MOD_RES
<222> LOCATION: (32)..(32)
<223> OTHER INFORMATION: amidation

<400> SEQUENCE: 14

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Thr Tyr
                20                  25                  30
```